United States Patent [19]

Eisert et al.

[11] Patent Number: 6,015,577

[45] Date of Patent: Jan. 18, 2000

[54] PHARMACEUTICAL COMPOSITIONS CONTAINING DIPYRIDAMOLE OR MOPIDAMOL AND ACETYLSALICYLIC ACID OR THE PHYSIOLOGICALLY ACCEPTABLE SALTS THEREOF, PROCESSES FOR PREPARING THEM AND THEIR USE IN TREATING CLOT FORMATION

[75] Inventors: Wolfgang Eisert; Peter Gruber, both of Biberach, Germany

[73] Assignee: Dr. Karl Thomae GmbH, Biberach an der Riss, Germany

[21] Appl. No.: 08/421,351

[22] Filed: Apr. 12, 1995

Related U.S. Application Data

[63] Continuation of application No. 08/261,789, Jun. 20, 1994, abandoned, which is a continuation of application No. 08/003,909, Jan. 13, 1993, abandoned, which is a continuation of application No. 07/879,258, May 6, 1992, abandoned, which is a continuation of application No. 07/750,345, Aug. 27, 1991, abandoned, which is a continuation of application No. 07/584,393, Sep. 18, 1990, abandoned, which is a continuation of application No. 07/423,108, Oct. 18, 1989, abandoned, which is a continuation of application No. 07/240,981, Sep. 6, 1988, abandoned, which is a continuation of application No. 07/084,648, Aug. 12, 1987, abandoned.

[30] Foreign Application Priority Data

Aug. 13, 1986 [DE] Germany .............................. 36 27 423

[51] Int. Cl.[7] .............................. A61K 9/36; A61K 9/58; A61K 9/62; A61K 31/62

[52] U.S. Cl. .......................... 424/451; 424/452; 424/457; 424/458; 424/461; 424/462; 424/479; 424/494; 424/495; 424/497; 424/474; 514/772.3; 514/781; 514/822; 514/824

[58] Field of Search ..................................... 424/464, 458, 424/461, 462, 494, 497, 474, 479, 451, 452, 495, 457; 514/822, 824

[56] References Cited

U.S. PATENT DOCUMENTS

| | | | |
|---|---|---|---|
| 4,367,217 | 1/1983 | Gruber et al. | 424/19 |
| 4,694,024 | 9/1987 | Weithmann et al. | 514/161 |

FOREIGN PATENT DOCUMENTS

| | | |
|---|---|---|
| A-2 368 280 | 5/1978 | France . |
| B-2 368 272 | 5/1978 | France . |
| B-2 390 959 | 12/1978 | France . |
| A-3 000 979 | 7/1981 | Germany . |
| A1-3 515 874 | 1/1986 | Germany . |

OTHER PUBLICATIONS

Lancet 1979, Dec. 8: 1213–1216.
Prostaglandins and Medicine, 4, 439–447, 1980.
Prostaglandins, Leukotrienes and Medicine, 12: 235–244, 1983.
Lancet 1987, Dec. 12;2(8572):1351–4.
Thromb Res 1998 Sep. 15;92(1 Suppl 1);S1–6.
Neurology 1998 Sep.;51(3 Suppl 3):S17–9.
Neurology 1998 Sep.;51(3 Suppl 3):S15–6.

*Primary Examiner*—Thurman K. Page
*Assistant Examiner*—James M. Spear
*Attorney, Agent, or Firm*—Robert P. Raymond; Alan R. Stempel; Mary-Ellen M. Devlin

[57] ABSTRACT

The specification describes a pharmaceutical combination consisting of dipyridamole or mopidamol and acetylsalicylic acid or the physiologically acceptable salts thereof, processes for preparing this pharmaceutical combination and the use thereof for the controlled prevention of clot formation.

20 Claims, 11 Drawing Sheets

PHARMACEUTICAL COMPOSITIONS CONTAINING DIPYRIDAMOLE OR MOPIDAMOL AND ACETYLSALICYLIC ACID OR THE PHYSIOLOGICALLY ACCEPTABLE SALTS THEREOF, PROCESSES FOR PREPARING THEM AND THEIR USE IN TREATING CLOT FORMATION

This is a continuation of application Ser. No. 261,789, filed Jun. 20, 1994, now abandoned which is a continuation of application Ser. No. 003,909, filed Jan. 13, 1993, now abandoned, which is a continuation of application Ser. No. 879,258, filed May 6, 1992, now abandoned, which is a continuation of application Ser. No. 750,345, filed Aug. 27, 1991, now abandoned, which is a continuation of application Ser. No. 584,393, filed Sep. 18, 1990, now abandoned, which is a continuation of application Ser. No. 423,108, filed Oct. 18, 1989, now abandoned, which is a continuation of application Ser. No. 240,981, filed Sep. 6, 1988, now abandoned, which is a continuation of application Ser. No. 084,648, filed Aug. 12, 1987, now abandoned.

The invention relates to pharmaceutical combinations consisting of dipyridamole or mopidamol and acetylsalicylic acid (aspirin) or the physiologically acceptable salts thereof, processes for preparing these pharmaceutical combinations and their use in the controlled prevention of clot formation.

It is known that acetylsalicylic acid, being an inhibitory substance, counteracts the aggregation of human blood platelets (cf. Br. J. Clin. Pharmac. 7 (1979) 283). It has been reported that acetylsalicylic acid inhibits the enzyme cyclooxygenase in the blood platelets and thus inhibits the biosynthesis of the aggregation-promoting thromboxane $A_2$. As the dosage increases, admittedly the antithrombotic activity of acetylsalicylic acid is increased but at the same time its inhibitory effect on the cyclooxygenase of the blood vessel walls is also increased, which indirectly has a negative influence on the synthesis of the aggregation-inhibiting substance prostacyclin. It is suggested (cf. Lancet, III (1979) 1213, Prostaglandins and Medicine 4 (1980) 439) that the lowest possible doses of acetylsalicylic acid be used. On the other hand, however, it is recommended (Prostaglandins, Leukotrienes and Medicine 12 (1983) 235) that higher doses be used since, as the dosage increases, the antithrombotic activity of acetylsalicylic acid is increased even if the biosynthesis of prostacyclin and thromboxane is already inhibited.

Dipyridamole (2,6-bis-(diethanolamino)-4,8-dipiperidino-(5,4-d)-pyrimidine) and mopidamol (2,6-bis-(diethanolamino)-8-piperidino-(5,4-d)-pyrimidine) are clinically used, inter alia, as active substances with an antithrombotic and antiaggregatory activity and mopidamol is also used as a metastasis inhibitor.

FR-B-2 368 272 describes a combination of dipyridamole and acetylsalicylic acid, preferably in a weight ratio of from 4:1 to 1:4, which has a synergistic effect on the thrombocyte aggregation induced. Since the two components are chemically incompatible with each other it was proposed that they be separated spatially from one another, e.g. by manufacturing so-called layered tablets or coated-core tablets.

A known preparation is Asasantin® made by Dr. Karl Thomae GmbH, Biberach/Riss, containing 330 mg of acetylsalicylic acid as well as 75 mg of dipyridamole; other possible combinations of other pyrimido-pyrimidines with acetylsalicylic acid in ratios of 0.5 and below are also already known (cf. FR-B-2 390 959).

DE-A1-3 515 874 (which is equivalent to U.S. Pat. No. 4,694,024) describes combined preparations containing pyrimido-pyrimidines, particularly dipyridamole and/or mopidamol, and acetylsalicylic acid or salts of these substances, wherein the weight ratio of the pyrimido-pyrimidine component to the acetylsalicylic acid component is greater than 0.5 and the pyrimido-pyrimidine component is released (made bioavailable) first. This can be achieved, for example, by using pharmaceutical carriers and excipients which ensure that the two components are released at different times. According to the statements made in that publication the medicinal effect is only obtained if, during successive (sequential or consecutive) administration, the relative proportion of acetylsalicylic acid is such that the weight ratio of pyrimido-pyrimidine to acetylsalicylic acid is maintained at not less than 0.5. The weight ratio of pyrimido-pyrimidine to acetylsalicylic acid should be more than 0.5 and up to 30. It should preferably be between 0.6 and 3. The interval between the release of the pyrimido-pyrimidine component and the acetylsalicylic acid component must be from 15 minutes to 2 hours, preferably from 30 minutes to 90 minutes, more especially between 40 and 70 minutes. According to that specification, it is possible to reduce the dosage of the individual components substantially, owing to a super-additive effect, to a point far below the dosages which would be required to achieve the same effects by administering acetylsalicylic acid or pyrimido-pyrimidine alone or by administering acetylsalicylic acid and pyrimido-pyrimidine together simultaneously.

It has now been found that a combination of dipyridamole and/or mopidamol or the physiologically acceptable salts thereof and acetylsalicylic acid or the physiologically acceptable salts thereof, containing the two components in a weight ratio of more than 4.5, preferably more than 5, and which releases the two components simultaneously in the gastrointestinal tract significantly reduces or prevents clotting and at the same time will dissolve any clot already present more rapidly than would occur through natural thrombolysis. In many cases, depending on the cause of the clotting, it may even be advantageous if, from a combination of this kind, first the acetylsalicylic acid were released, followed by pyrimido-pyrimidine at a later stage in the gastrointestinal tract. The time interval in question might be from 15 to 90 minutes. The upper limit for the ratio of pyrimido-pyrimidine to acetylsalicylic acid may be regarded as 100, primarily for practical reasons, but this upper limit should not be regarded as critical for the interaction of the two components. The pyrimido-pyrimidine content is limited, for example in the case of preparations which are to be swallowed, such as plain or coated tablets, by the fact that these preparations would be too bulky if the pyrimido-pyrimidine content were increased further.

The two components, pyrimido-pyrimidine and acetylsalicylic acid, may be present as a mixture which is particularly suitable for the preparation of instant forms, the two components being separated from each other, and hence made suitable for long storage, by the application of a suitable protective layer. As is well known, the component acetylsalicylic acid is not free from traces of acetic acid which are formed by cleavage of the acetylsalicylic acid during storage. The free acetic acid reacts with the dipyridamole to form hygroscopic salts and dipyridamole-acetic acid esters which cause the dipyridamole to spoil. These processes in the dipyridamole can be prevented by providing one or other or both of the components with a separating layer. Thus, for example, dipyridamole in the form of pellets or granules is provided with a coating which is insoluble in gastric juices but soluble in intestinal juices and/or the acetylsalicylic acid cores or tablets are provided with a coating which is resistant to acetic acid and is very quickly dissolved in the gastric juices. The same also applies to mopidamol.

However, it is also possible, for example, to prepare a dipyridamole granulate, a separating granulate and an acetylsalicylic acid granulate separately and then compress them to form three-layer tablets; a pyrimido-pyrimidine granulate, however, may also be packed into a capsule together with a coated tablet provided with a protective coating, or a film-coated tablet, containing the acetylsalicylic acid. If, on the other hand, it is particularly important to obtain a constant level of pyrimido-pyrimidine in the blood, it will be advantageous to start with pyrimido-pyrimidine pellets which enable this active substance to be released at a steady rate with a controlled pH, and these pellets are processed together with the acetylsalicylic acid to form corresponding drug preparations. It may be advantageous to produce compressed tablets of acetylsalicylic acid with a suitable covering of a film coating and combine them with the pyrimido-pyrimidine pellets. If it is intended that the acetylsalicylic acid should be released first, the pyrimido-pyrimidine pellets may be coated with a coating which delays the release of this active substance and the cores containing the acetylsalicylic acid coated with a coating which is soluble in gastric juices. In the case of dipyridamole pellets with a controlled release of the active substance it is particularly advantageous to use pellets prepared according to the instructions given in (DE-A-3000979.1 (which is equivalent to U.S. Pat. No. 4,367,217). These pellets have a coating which acts as a dialysis membrane and releases the active substance dipyridamole in conjunction with acids in the gastrointestinal tract in a regulated delayed manner. The construction and composition of the pellets causes the dissolved dipyridamole to be released in the form of its salts. Delayed release pellets produced in this way ensure that the dipyridamole is fully reabsorbed from the gastrointestinal tract. This ensures constant blood levels over a period of 8 to 10 hours, avoiding any peaks, such as frequently occur with the dipyridamole-acetylsalicylic acid preparations currently on sale (e.g. according to FR-B-2 368 272). The blood level peaks observed with the preparations according to this French patent specification stem from the fact that dipyridamole is resorbed only partially and to different extents in individual cases. In many patients the blood level values fall below the effective range after a short time or, in some cases, are never attained (in so-called "non-absorbers"); the acetylsalicylic acid will, on the other hand, achieve its full pharmacological activity in every patient.

A preferred object of this invention thus relates to pharmaceutical preparations consisting of dipyridamole and/or mopidamol in conjunction with a physiologically acceptable acid, with at least 1 equivalent of acid to 1 mol of dipyridamole or mopidamol, surrounded by a coating made up of 50 to 100% of lacquers which are insoluble in acid but soluble in intestinal juices and 50 to 0% of lacquers which are insoluble in both gastric and intestinal juices, this component occurring in the form of granules or pellets, and the component acetylsalicylic acid, which is preferably provided with a coating which is soluble in gastric juices and preferably in the form of a sugar-coated or film-coated tablet, the two components being present in a weight ratio of at least 4.5.

Whereas preferred preparations according to DE-Al-3 515 874 have a weight ratio of pyrimido-pyrimidine to acetylsalicylic acid of between 0.6 and 1.5 (any ratios beyond these figures are not illustrated by Examples), these weight ratios in the present invention are over 4.5, preferably from 8 to 100.

The pharmaceutical preparations contain between 10 and 675 mg of dipyridamole and/or mopidamol and between 1 and 150 mg of acetylsalicylic acid. As for dipyridamole and mopidamol, preferred preparations contain between 75 and 400 mg of this active substance, particularly preferred preparations contain between 75 and 200 mg together with 5 to 80 mg or 5 to 40 mg of acetylsalicylic acid. Generally, two to three of these dosage units are administered per day, although deviations above and below this dosage are possible depending on the severity of the condition. The dosage to be used naturally also depends on other factors, e.g. the age, weight and general health of the patient being treated, the gravity of the symptoms or the disease.

The pharmaceutical preparations according to the invention may optionally contain other conventional carriers and/or excipients and are prepared by methods which are conventional per se. Conventional carriers and/or excipients which may be used include, for example, potato, corn or wheat starch, cellulose, cellulose derivatives, silicon dioxide, various sugars, and as coating substances sugar and/or starch syrup, gelatin, gum arabic, polyvinylpyrrolidone, synthetic cellulose esters, surfactants, plasticisers and/or pigments and similar additives and, for the preparation of tablets and tablet cores, lubricants such as magnesium stearate.

In order to prepare a dipyridamole granulate according to the invention, dipyridamole is mixed, for example, with an organic edible acid such as fumaric, tartaric, citric, succinic or malic acid and with binders and/or adhesives such as polyvinylpyrrolidone, then a lubricant such as magnesium stearate is added, the mixture is compressed, e.g. using a roller compactor, and then broken up into granules, e.g. using a dry granulating apparatus with an adjoining screening mechanism.

Dipyridamole pellets are preferably produced using starter cores which advantageously consist of an organic edible acid, e.g. rounded tartaric acid crystals (diameter of the starter cores 0.5 to 0.9 mm), onto which a suspension of dipyridamole in an alcohol or alcohol/water mixture and a binder such as polyvinylpyrrolidone is sprayed in a pan until the resulting pellets of active substance contain the prescribed quantity of dipyridamole (the pellets will then have a diameter between 0.9 and 1.5 mm). If a delayed release of active substance is envisaged, these pellets are then coated with a lacquer consisting of 50 to 100% of lacquers which are acid-insoluble but soluble in the intestinal juices and 50 to 0% of lacquers which are insoluble in both gastric and intestinal juices. A lacquer consisting of methacrylic acid/methacrylic acid ester copolymers (Eudragit S®) and hydroxypropylmethylcellulose phthalate (HP 55®) to which plasticisers and fillers such as talc may be added, has proved suitable. Lacquer components which are soluble in intestinal juices include cellulose acetate phthalate, ethylcellulose phthalate, hydroxypropylmethylcellulose succinate, cellulose acetate succinate, hydroxypropylmethylcellulose hexahydrophthalate, cellulose acetate hexahydrophthalate, hydroxypropylmethylcellulose trimellitate, methacrylic acid/methacrylic acid ester copolymer (acid number 300 to 330, Eudragit L®) or mixtures of these substances. Lacquers which are insoluble in both intestinal and gastric juices, to be added to the mixture, may be: lacquers based on acrylate or methacrylate (Eudragit retard S® and Eudragit retard L®), also combined with up to 14% by weight of ethylcellulose.

Dipyridamole (and/or mopidamol) pellets may, however, also be obtained by feeding a powdered mixture of dipyridamole (and/or mopidamol) and the calculated quantity of an organic edible acid (e.g. fumaric acid) and binders and optionally other excipients into an extruder (e.g. a double screw extruder), then feeding in an organic solvent and thoroughly mixing the mass. The moist mass is extruded in the form of spaghetti which is rounded off on a rapidly rotating plate to form highly compressed pellets. The pellets are then dried and, optionally, coated with a retarding lacquer as described above.

The acetylsalicylic acid may be used in the form of compressed cores which are coated with an isolating covering layer or in the form of film-coated tablets. The cores are produced from acetylsalicylic acid, lubricants and carriers and/or diluents, such as free-flowing lactose, microcrystalline cellulose, dried corn starch, aluminium or magnesium stearate, in known manner by preparing and compressing a suitable granulate. The cores are coated, possibly in several steps, with a coating suspension consisting, for example, of sugars (such as sucrose), gum arabic, talc and similar substances.

A typical three-layer tablet is obtained, for example, by compressing a pyrimido-pyrimidine granulate, an acetylsalicylic acid granulate and a separating granulate, made up of lactose, microcrystalline cellulose and polyvinylpyrrolidone, for example, and containing a lubricant, using a special tablet press with three filling hoppers and three compressing stations, in such a way that the neutral separating layer is located between the two compressed active substances.

The combination according to the invention is used as an antithrombotic agent which inhibits blood platelet aggregation and metastasis in humans and animals; the combination prevents the formation and persistence of venous and arterial blood clots and thus prevents temporary ischaemic episodes and helps to prevent cardiac infarction and strokes. It is highly suitable for preventing the formation and persistence of clots in the case of arteriosclerosis or after operative intervention or other conditions which involve a tendency to thrombosis; however, when the combination is administered, the typical properties of the individual components also come into effect, e.g. there is an improved $O_2$ supply to the heart muscles and there is some inhibition of inflammatory processes and also an alleviation of pain.

In vivo tests on the rat

The antithrombotic activity achieved with a simultaneous oral administration, according to the invention, of 5 mg/kg of dipyridamole and 0.05 mg/kg of acetylsalicylic acid (weight ratio of dipyridamole to acetylsalicylic acid=100) and, by comparison, during sequential oral administration (according to European Application No. 85 108 761.9) of 5 mg/kg of dipyridamole and 5 mg/kg of acetylsalicylic acid to rats (FW 49) with a body weight of from 60 to 80 g before the start of the experiment was investigated by applying a clotting stimulus to vessels of the mesenterium and by monitoring the size of the clots over a period of time. Groups of 5 animals were used. A standardised stimulus led to a clot of a size which occluded 80% of the diameter of the blood vessel. An interval of 1 hour was left between the simultaneous oral administration of the substances according to the invention and the application of the clot or the actual carrying out of the measurements. The sequential oral administration of the substances according to the European application specified hereinbefore was effected by administering dipyridamole 90 minutes before the acetylsalicylic acid was administered and administering the latter 60 minutes before the clot was produced and the measurements began; in other words, dipyridamole was given 150 minutes before the start of the experiment and acetylsalicylic acid was given 60 minutes before the start of the experiment.

In order to perform the experiment the animals were anaesthetised with about 60 mg/kg of nembutal i.p., their abdomens were opened up and part of the mesenterium was dislocated outwards and rinsed with warmed physiological nutrient solution whilst the measurements were taken.

Using an intravital microscope to monitor the process, a platinum electrode was placed on an outer blood vessel wall of the mesenterium. A counter-electrode was pushed under the mesenterium. A fixed combination of a direct voltage (150 V) and current (1.5 mA) 35 in a pulse of a given length (100 ms) leads to the reproducible formation of a clot, in a vein about 300 $\mu$m in diameter, which will generally occlude 80% of the diameter of the vein. The size of the clot is measured at 10 second intervals and later at 30 second intervals over a period of up to 20 minutes after the stimulation of the blood vessel and is given as the size of the clot (at right angles to the blood vessel wall) as a percentage of the internal diameter of the blood vessel.

BRIEF DESCRIPTION OF THE DRAWINGS

Within the observation period of 20 minutes, a stable clot size of about 85% is observed by comparison with the controls, which consist of animals treated only with the solvent or carrier in question, administered orally (cf. FIG. 7, N-68 control measurements; averages at each separate time, the standard deviation being specified [±SD].

Acute occlusion of the blood vessels, such as occurs in cardiac infarction or in strokes, is generally held to be caused by a rapidly forming clot at the site of an existing injury or some pathological change to the blood vessel wall. Medication which inhibits clot formation ensures that the clot formed does not reach levels of 85% of the diameter of the blood vessel, the size achieved in the control group. This is the only way of preventing unrestricted clot formation from blocking the blood flow, which conventionally has serious consequences as a result of the ischaemic damage caused (e.g. cardiac infarction or stroke). Medication using a substance or combination of substances which results only in rapid dissolution of a clot will generally allow the clot to form up to a size comparable with that of the control group but will then significantly reduce the size of the clot in the succeeding test interval, i.e. it will not prevent initial blockage of the blood flow. FIGS. 1 and 2 show the behaviour of the size of the clot over a period of time after electrical stimulation of the clot after administration of a combination according to European Patent Application No. 85 108 761.9 referred to above (FIG. 1) and a combination according to the invention (FIG. 2).

FIG. 1 shows the pattern of the clot size within 20 minutes of the production of the clot after oral administration of 5 mg/kg of acetylsalicylic acid 60 minutes before the measurement is carried out and an oral administration of 5 mg/kg of dipyridamole 150 minutes before the measurement is carried out. In the control group the size of the clot remains at about 85% during the first half of the observation period and then falls slightly during the second half, whereas in the treated group the size of the clot assumes a value similar to that of the control test in the first 30 seconds but then falls more sharply as the experiment continues.

FIG. 2 shows a significantly different pattern. Here, a control group is compared with a group which was given 5 mg/kg of dipyridamole and 0.05 mg/kg of acetylsalicylic acid simultaneously, according to the invention, 60 minutes before the start of the measurements. By contrast with FIG. 1, the treated group shows a significantly inhibited clot formation even at the beginning and during the first phase of the test and the size of the clot assumes values right at the start of the experiment which are only achieved in the middle third of the experiment in the treated group shown in FIG. 1.

It is apparent from these patterns in FIGS. 1 and 2 that the pre-treatment on which FIG. 2 is based has actually prevented the formation of a clot whereas the treatment on which FIG. 1 is based merely brings about faster dissolution of the clot formed, but this is also observed with the treatment on which FIG. 2 is based.

FIGS. 3 to 6 show the percentage clot sizes at individual times, by comparison with one another. Columns A represent the clot sizes of the control group, i.e. the clot size of the control group is taken as 100%. Columns B show the clot sizes obtained with a combination of 5 mg/kg of dipyridamole and 5 mg/kg of acetylsalicylic acid corresponding to the curve in FIG. 1, columns C show the clot sizes after previous administration of 2.5 mg/kg of acetylsalicylic acid, columns D show these clot sizes after previous administration of 5 mg/kg of dipyridamole and columns E show them after previous administration of the combination according to the invention of 5 mg/kg of dipyridamole and 0.05 mg/kg of acetylsalicylic acid corresponding to the curve in FIG. 2, whilst columns F show the results obtained with 2 mg/kg of dipyridamole and 0.05 mg/kg of acetyl-salicylic acid (all the substances are administered by oral route).

FIG. 3 shows the percentage reduction in the 85% occlusion in the period from 10 seconds to 1 minute after stimulation of the blood vessel, compared with the controls which are taken as 100%. As can be seen from this Figure, the size of the clot obtained by electrical stimulation is reduced by about 20% (i.e. is virtually already in statu nascendi) when the combination according to the invention is present (column E); after administration of the known combination (column B), however, it is reduced by only about 5%; this means that clot formation is significantly inhibited on administration of the combination according to the invention.

FIG. 4 shows the same conditions over the period from 2 to 4 minutes after stimulation. The clot size is gradually reduced and the reduction is most noticeable with the combination according to the invention.

FIG. 5 shows the conditions over the period from 5 to 10 minutes after stimulation, whilst FIG. 6 shows the period from 10 to 20 minutes. A reduction in the clot size corresponding to that obtained with the combination according to the invention is only achieved about 15 minutes after stimulation, with the known combination. Acetylsalicylic acid and dipyridamole on their own do not bring about any significant reduction in the clot size. If the percentage reductions are compared with one another, particularly in FIG. 6, it will become apparent that the combinations of acetylsalicylic acid and dipyridamole produce super-additive or synergistic effects. However, FIG. 3 also shows another inter-relation: when the acetylsalicylic acid dosage is increased relative to that of dipyridamole the inhibiting effect on clot formation is reduced; it has been found that, when combinations are administered containing weight ratios of dipyridamole to acetylsalicylic acid of less than 4, situations corresponding to the curve shown in FIG. 1 or to the values shown in columns B in FIGS. 3 to 6 are very rapidly arrived at. However, this clearly demonstrates that the combinations according to the invention are significantly superior to the known combinations in the prevention of clotting. Nor should it be overlooked that this effect is achieved with a combination in which the proportion of acetylsalicylic acid is very small, which means that the side effects of this substance should not occur.

Figure 1:
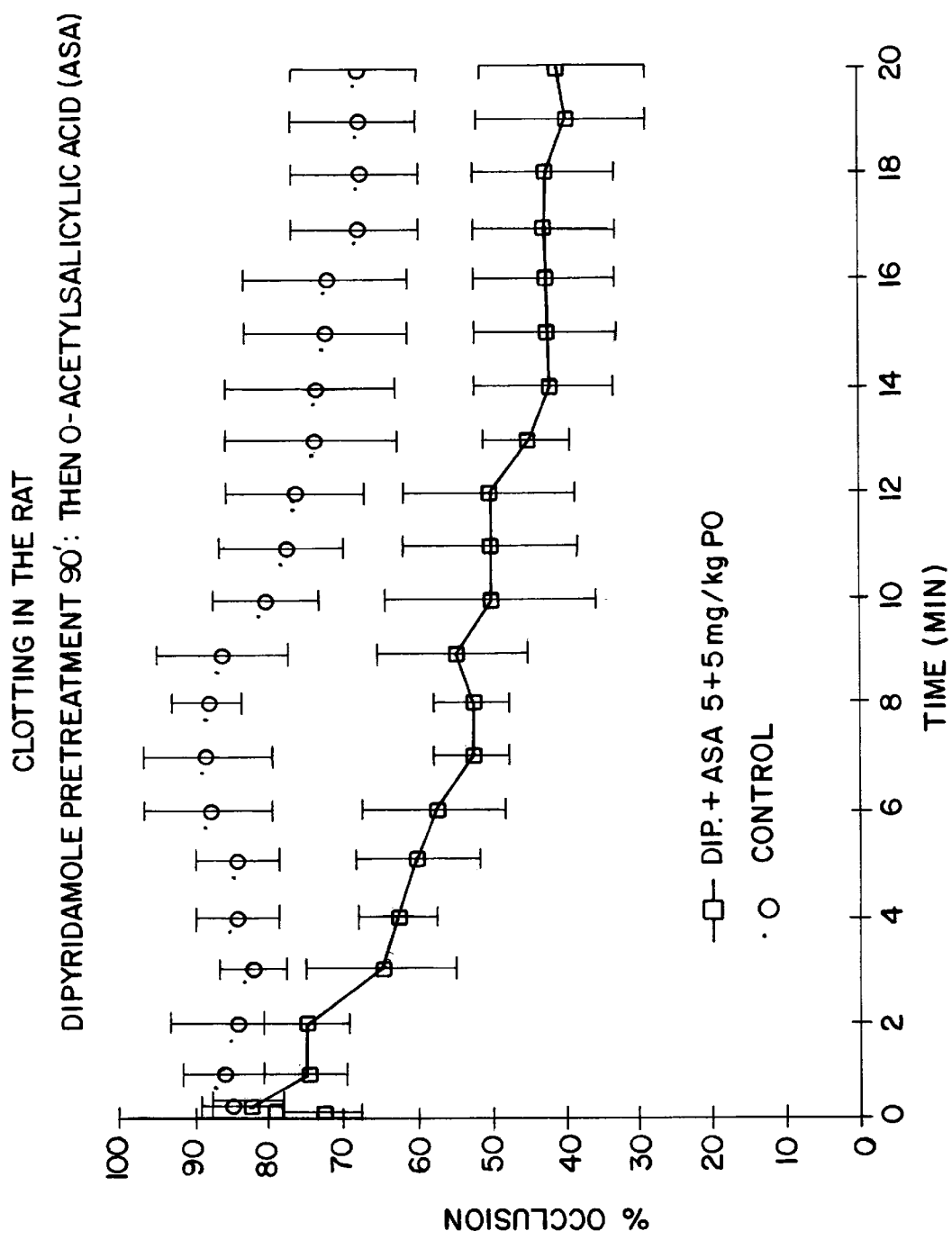
FIGS. 1–11 graphically illustrate the effects the drug combinations have on blood clotting in rats in comparison to controls.
Figure 2:
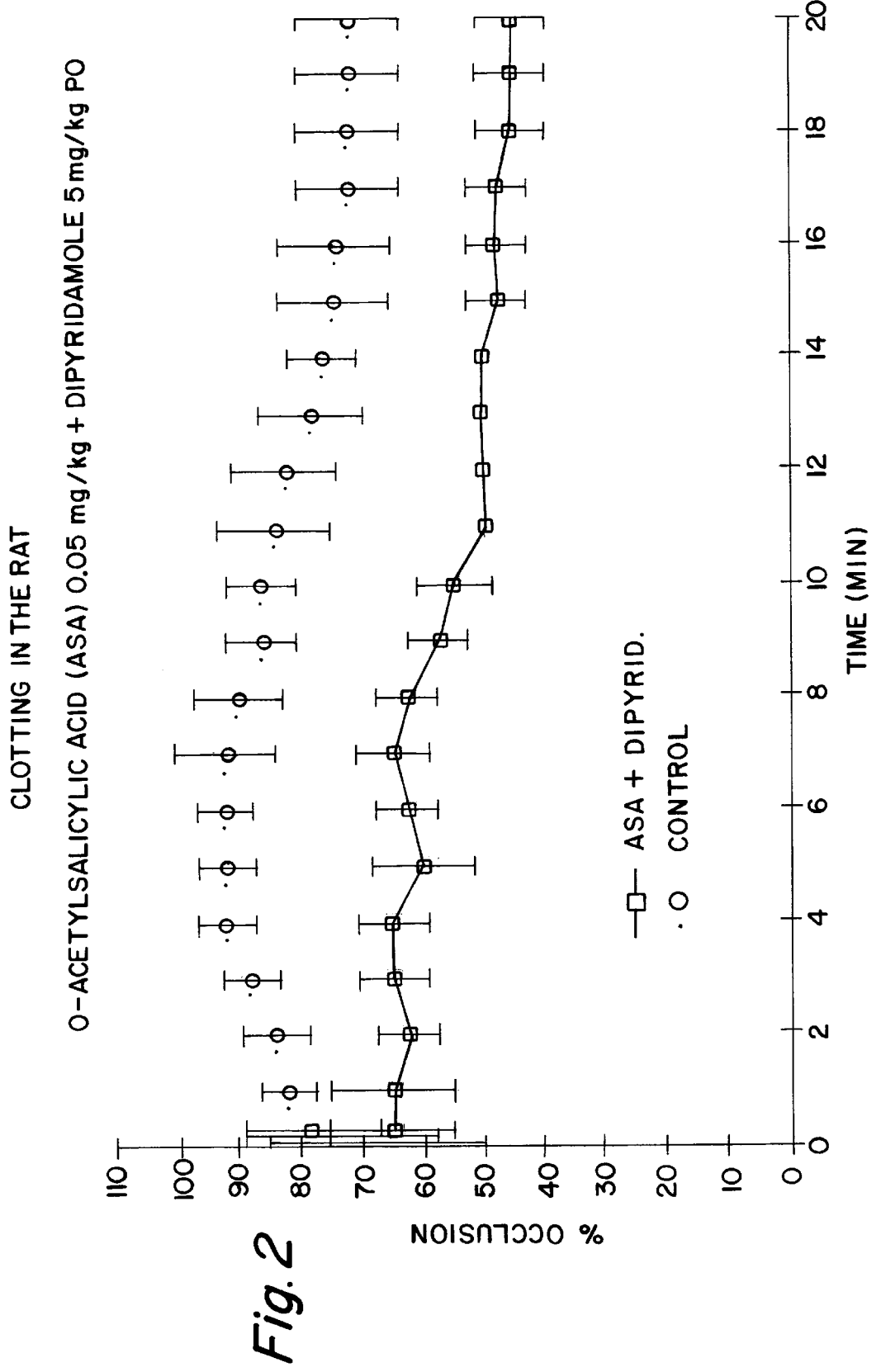
Figure 3:
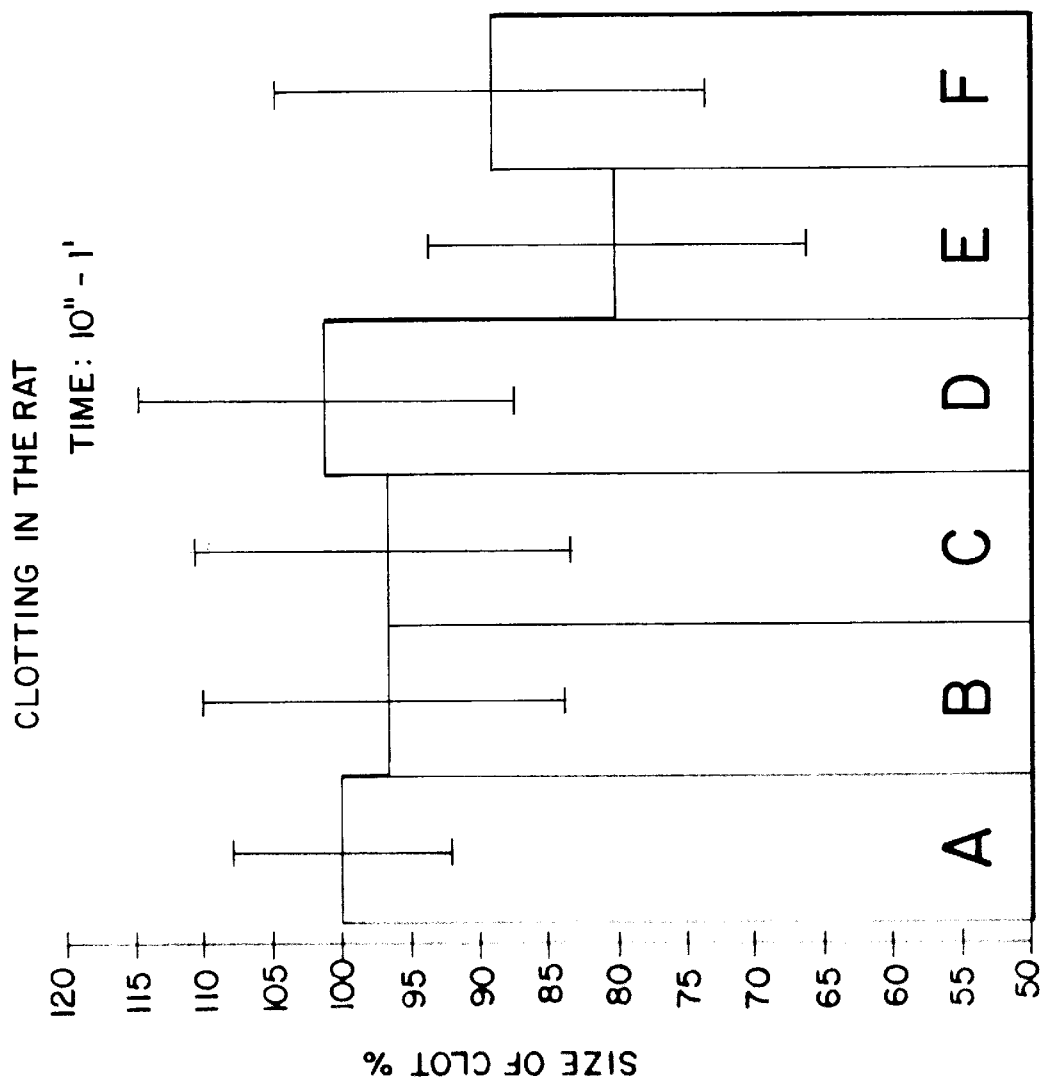
Figure 4:
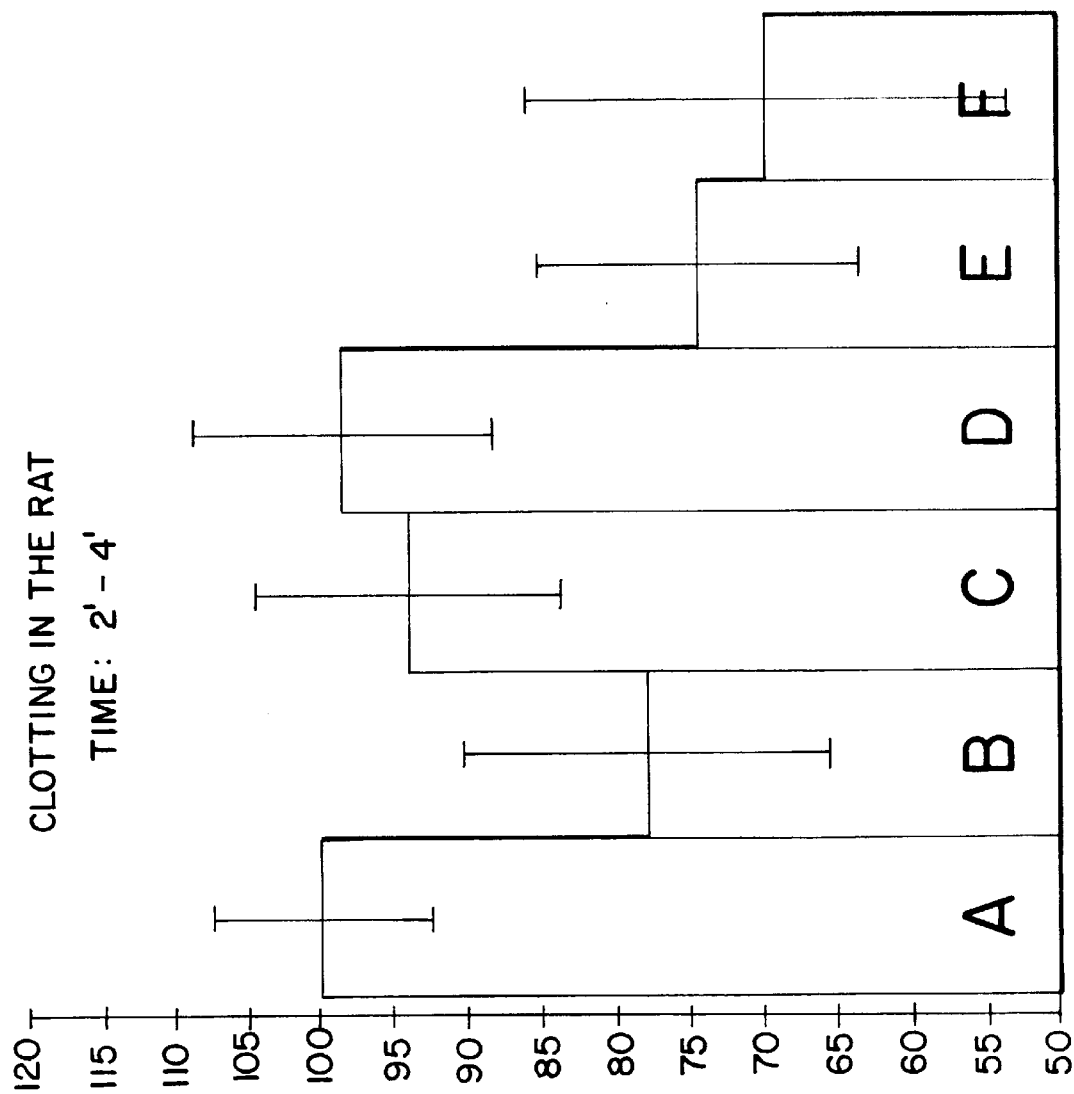
Figure 5:
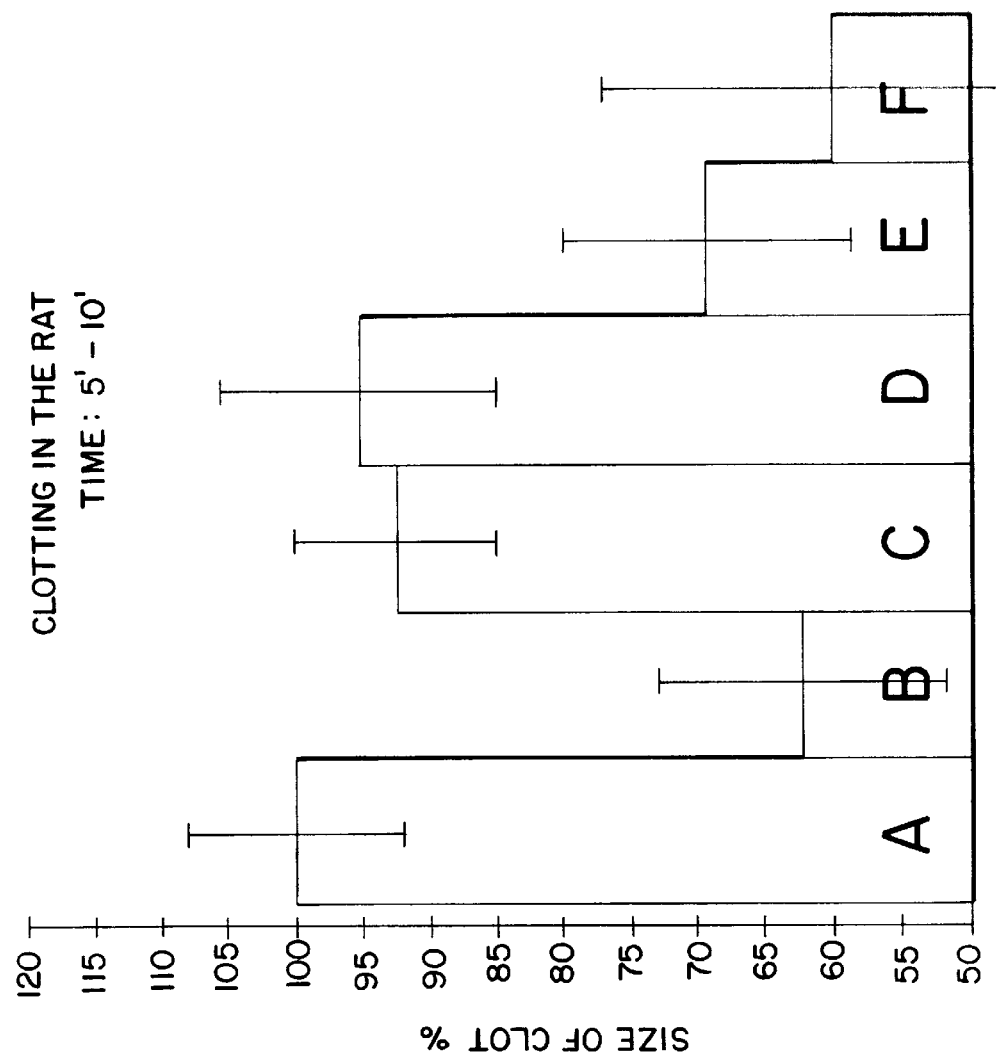
Figure 6:
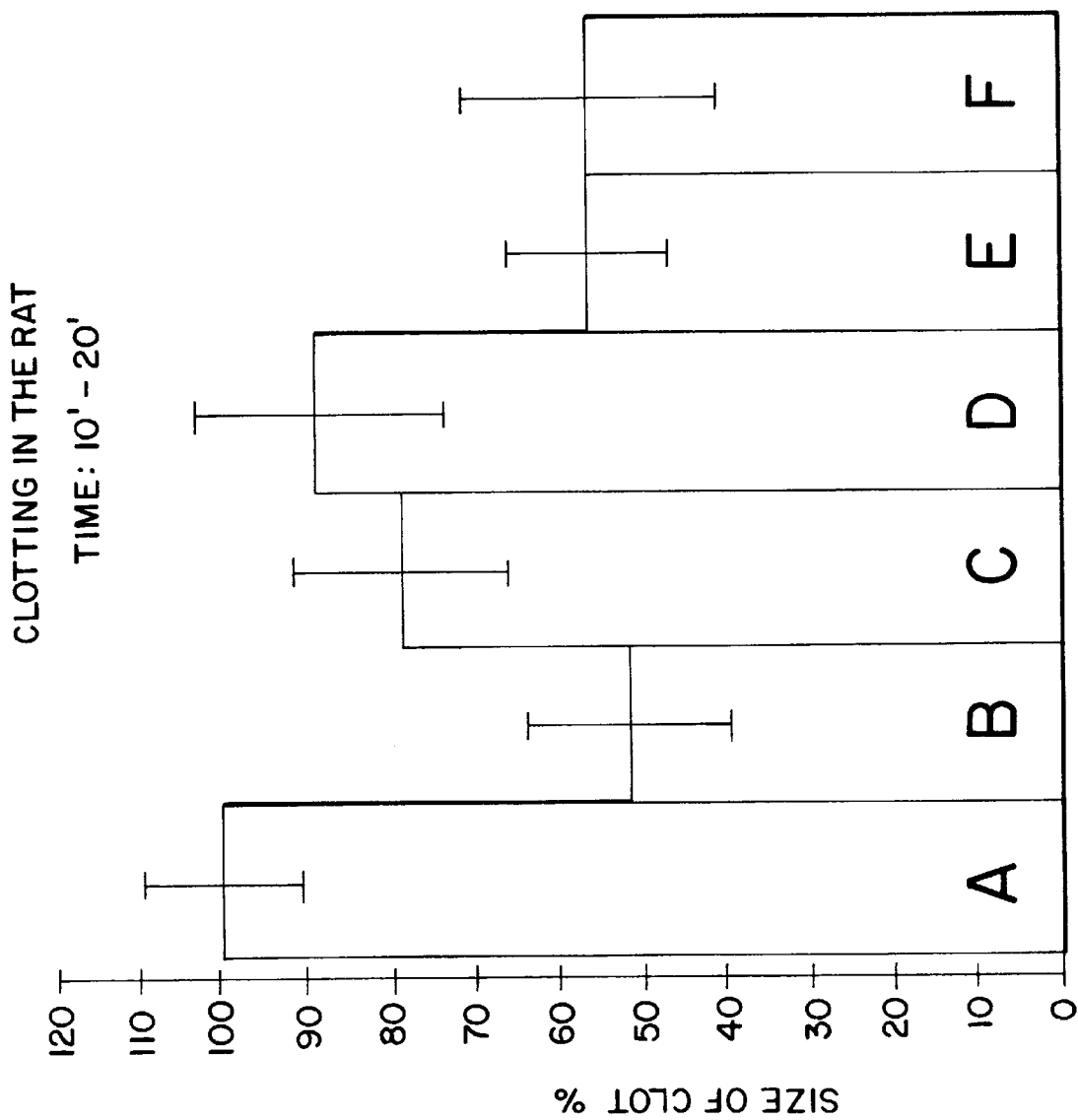
Figure 7:
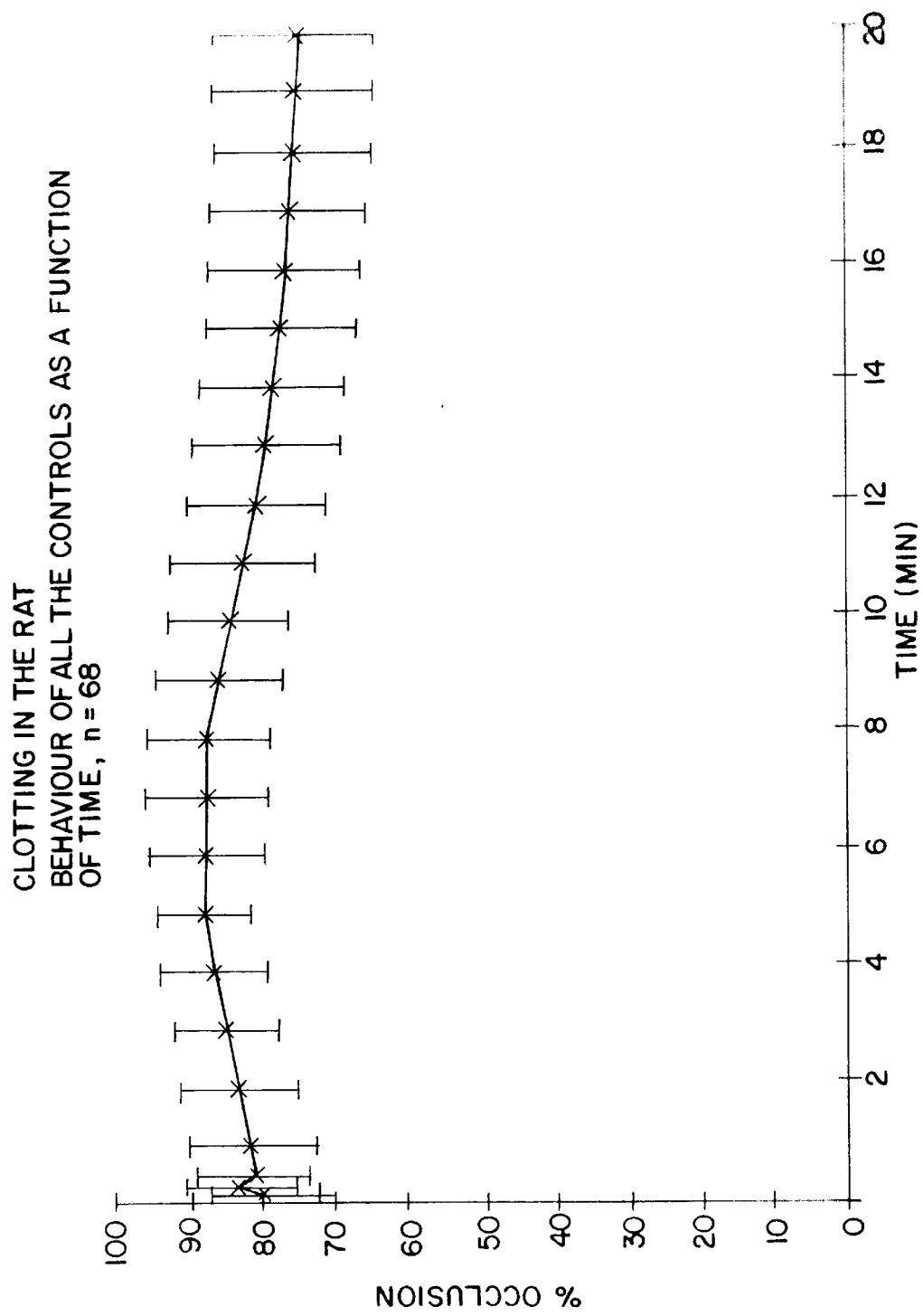

The fact that not only the sequence of the administration of dipyridamole and acetylsalicylic acid but also, when these substances are administered simultaneously, the ratio of dosages of the two active substances is of critical importance in preventing vascular blockage caused by clots was demonstrated by experiments on recurrent thrombosis in the rabbit aorta. Using the model of the circumflex artery in the dog, described by J. D. Folts in Circulation 54 (1976) page 365, a recurrent model using the abdominal aorta of the rabbit was developed. After being anaesthetised with Rompun, initially with 10 mg/kg of Rompun and 70 mg/kg of Ketanest i.m. and, continuously with 4 mg/kg/h of Rompun and 20 mg/kg/h of Ketanest i.m. throughout the experiment (by drip), rabbits (New Zealand Whites with a body weight of about 3 kg) were laparotomised by sagital section. The abdominal aorta was exposed distally of the renal artery; an electromagnetic flow probe was applied to the proximal end of this section (alternatively an ultrasonic flow probe could also be used). Distally of the flow probe the aorta was mechanically damaged by repeated pinching with an arterial clamp (a hemostat). This procedure resulted in damage to the artery by rupture of the lining of the lumen, exposure of subendothelial structure, connective tissue and smootn muscle. Mechanical stenosis is applied at the site of the vascular damage, reducing the flow through the aorta to about 40% of the original level.

After this damage it is observed that the total volume flow through the aorta is constantly reduced over a period of a few minutes until the flow ceases altogether. The vessel remains blocked until the clot formed in the constricted segment is released by mechanical agitation, i.e. is embolised. The original flow is thus restored. The blood flow then gradually decreases again until it comes to a standstill once more. After fresh mechanical agitation or embolising of the clot this recurrent process is repeated over and over again.

At the start of each experiment a number of flow reduction cycles is established over a period of 30 minutes for control purposes. Then the active substance which is being tested is administered either intravenously or into the mesenterial vein. The flow reduction cycles observed are maintained over a period of 30 to 60 minutes and over a further period of 60 to 90 minutes after administration of the active substance. An effective substance delays the stoppage of the blood flow, spontaneously embolises the clot formed in the stenosed segment or, if it is highly effective, reestablishes the original blood flow without any periodic reduction. The maximum attainable antithrombotic effect thus corresponds to total restoration of the maximum blood flow possible through the stenosis (100% free flow).

The pattern of flow reduction cycles before administration of the active substance is determined for comparison purposes in order to evaluate the results numerically. A flow pattern is constructed from the difference between the flow reduction rate and the amplitude of the cyclical flow oscillation, using a computer, to show the increase in free flow at any time after administration of the active substance. Mechanically induced clot embolisation is calculated negatively by comparison with spontaneous clot embolisation (i.e. there is no correction or, if necessary, positive correction). From these corrected curves the computer calculates the parameter of "free flow" for 20 or 30 minute intervals before and after administration of the active substance.

In order to minimise any topical effects which might arise on oral administration of acetylsalicylic acid, the active substances were administered as a bolus into the mesenterial vein.

Results:

100% free flow denotes unrestricted flow through the aorta unimpeded by clots (although with the mechanical constriction referred to above). Four animals were used for each group. The following dosages or combinations of dosage were used:

| | | |
|---|---|---|
| 1.) | Dipyridamole | 5 mg/kg |
| 2.) | Acetylsalicylic acid | 50 μg/kg |
| 3.) | Acetylsalicylic acid | 100 μg/kg |
| 4.) | Acetylsalicylic acid | 1 mg/kg |
| 5.) | Acetylsalicylic acid | 500 μg/kg |
| 6.) | Acetylsalicylic acid + Dipyridamole | 500 μg/kg + 5 mg/kg (FIG. 8) |
| 7.) | Acetylsalicylic acid + Dipyridamole | 50 μg/kg + 5 mg/kg (FIG. 9) |
| 8.) | Acetylsalicylic acid + Dipyridamole | 100 μg/kg + 5 mg/kg (FIG. 10) |
| 9.) | Acetylsalicylic acid + Dipyridamole | 5 mg/kg + mg/kg (FIG. 11) |

Figure 8:
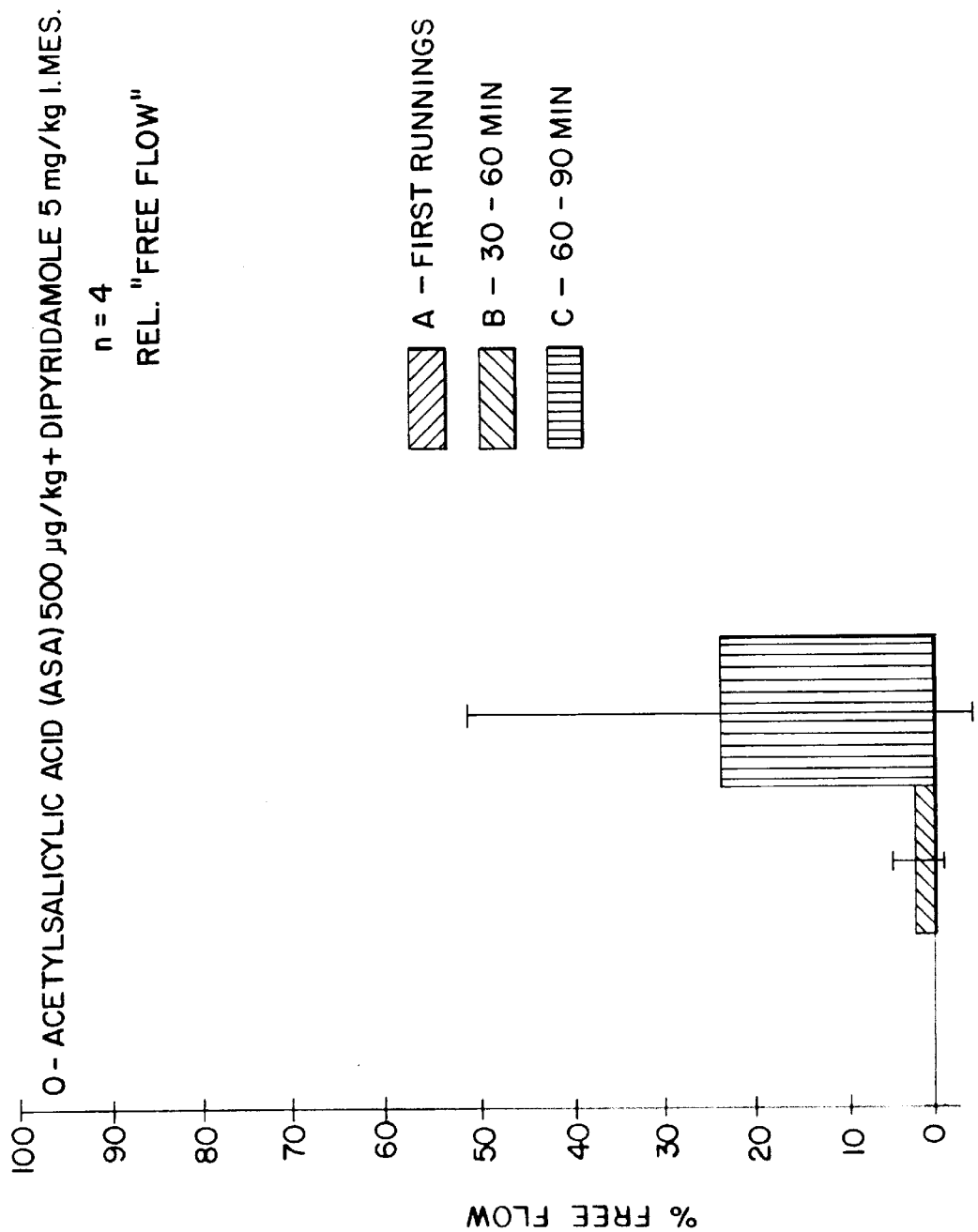
Figure 9:
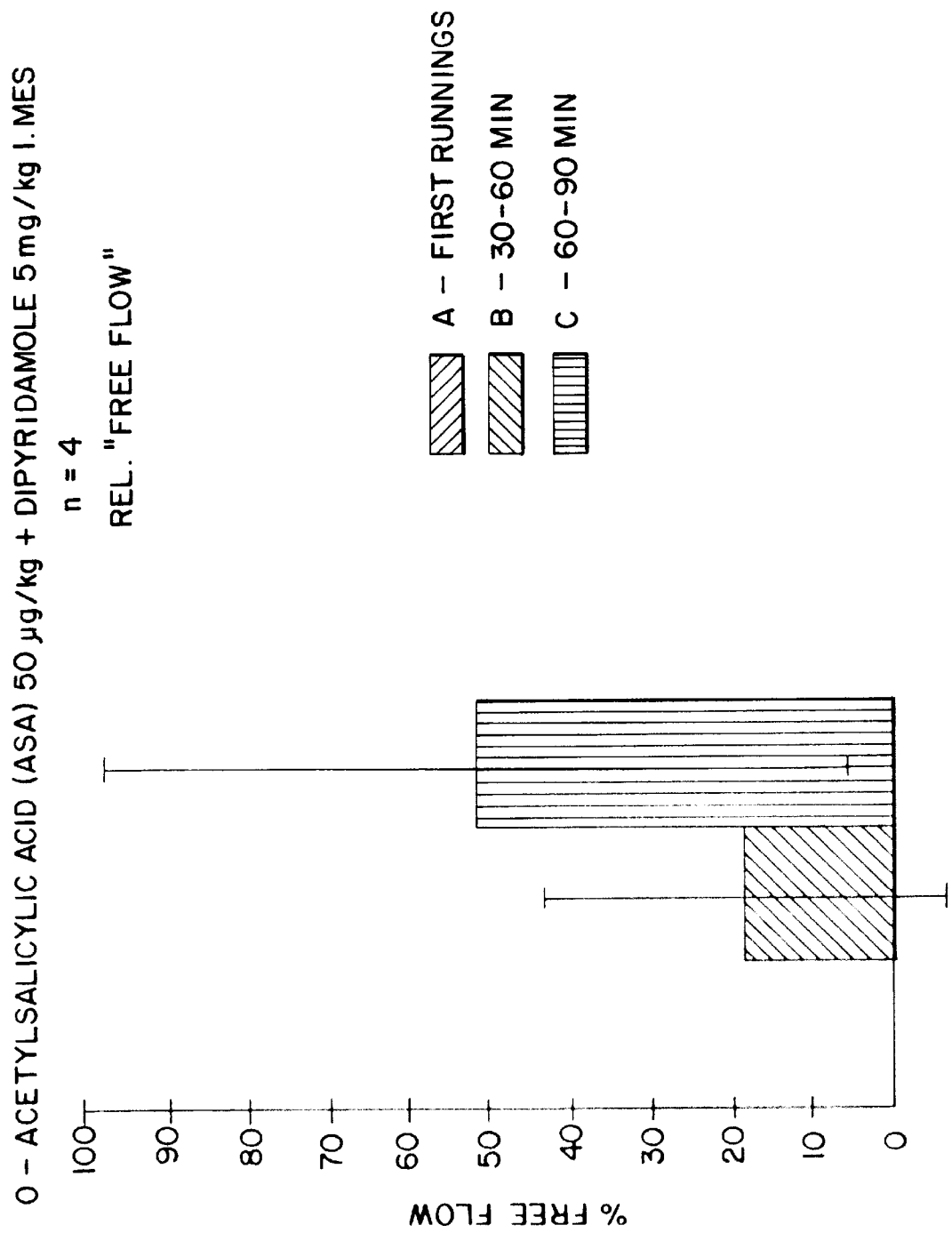
Figure 10:
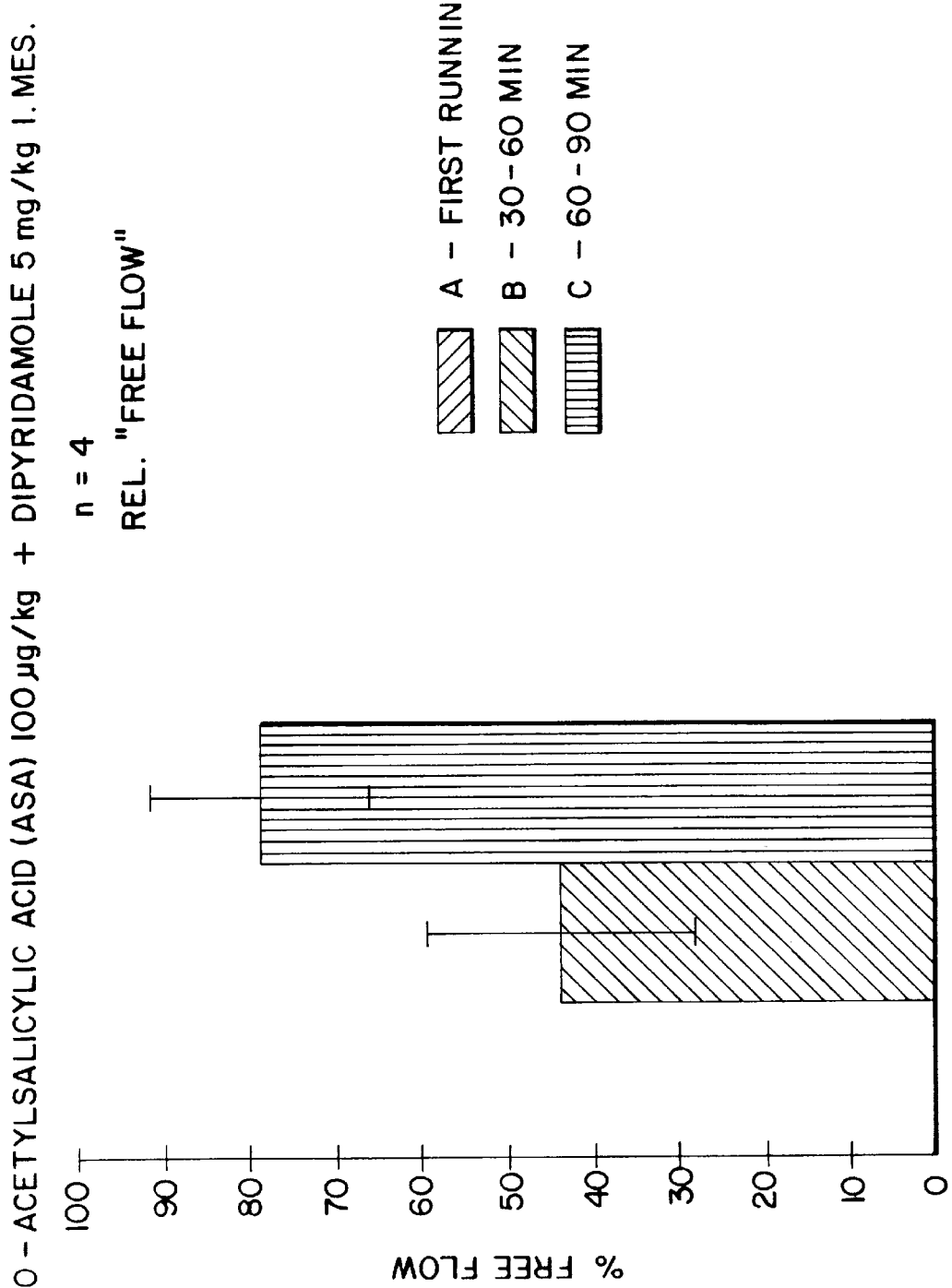

The first five treatments with single substances showed no effects at all in this experiment. Combinations of dipyridamole with acetylsalicylic acid administered simultaneously, on the other hand, showed an increase in free flow as time went on. Cf. FIGS. 8 to 10. These figures show that the ratio of dipyridamole to acetylsalicylic acid of 10:1 is less effective than that of 100:1, but the latter is in turn less effective than that of 50:1 in terms of an increase in free flow.

Figure 11:
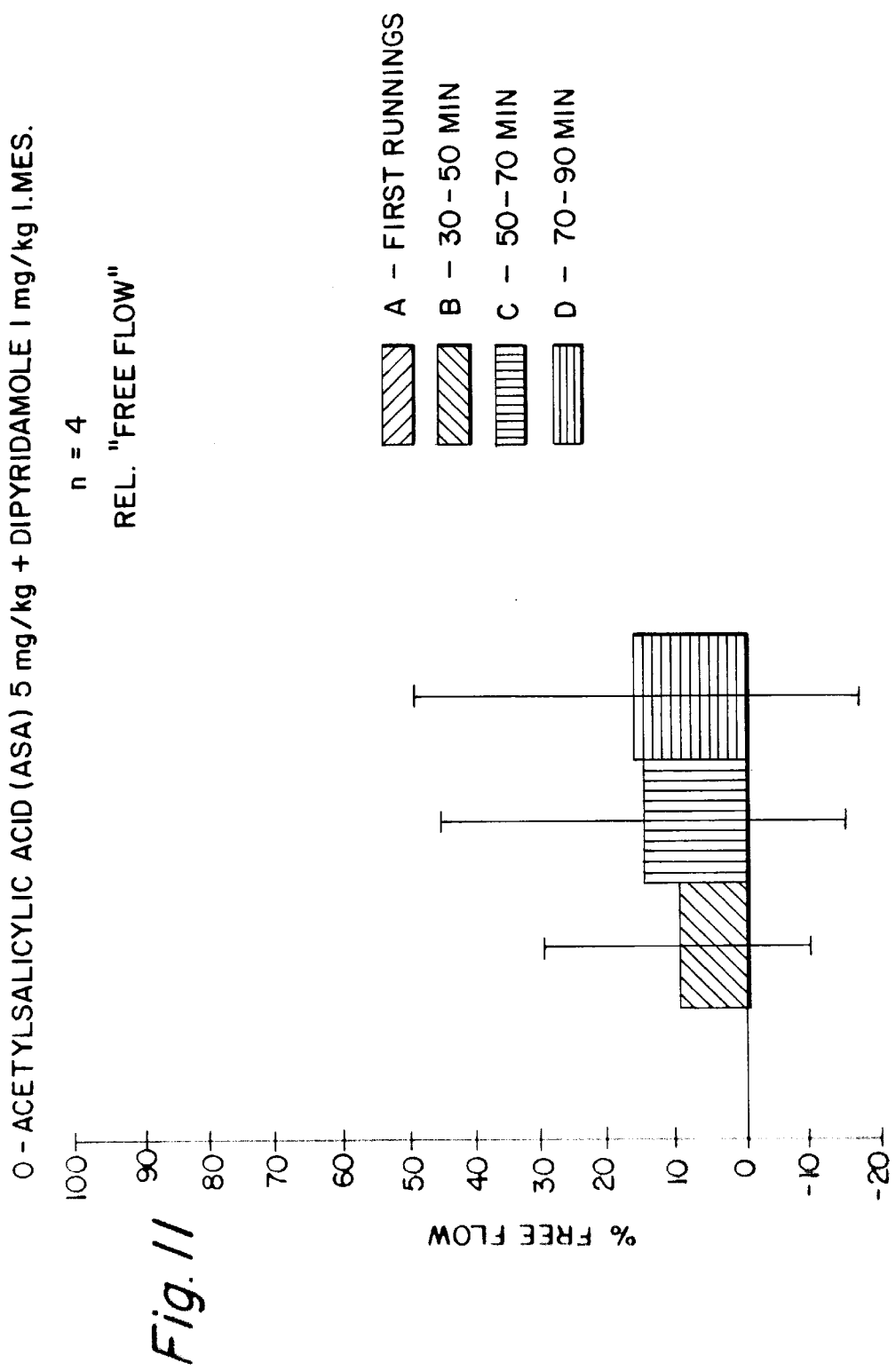

FIG. 11 shows the situation obtaining for a known combination (Asasantin®); it is apparent that this is significantly less effective than the combinations according to the invention. Since the combinations known hitherto always use comparatively high concentrations of acetylsalicylic acid, an increased risk of bleeding has hitherto repeatedly been pointed out. The combinations according to the invention demonstrate a surprisingly significantly improved activity at a substantially lower concentration of acetylsalicylic acid, which means that the risk of bleeding is very significantly reduced or even eliminated.

A combination of the two active substances begins to act even at the first stage of clot formation; the risk of recurrent thrombosis in a system with high pressure and high rates of flow and shear ("high flow/high pressure system") is significantly reduced. The preferred dosage is 50:1 (dipyridamole to acetylsalicylic acid) (in rabbits). However, it should not be forgotten that rabbits generally have a less sensitive response to antithrombotic treatment than other animals or humans. The experiments indicate that a combination of dipyridamole and acetylsalicylic acid prevents arterial clotting much more effectively than monotherapy. The superiority of treatment with a ratio of 100:1 as compared with a ratio of 10:1 in terms of preventing clotting confirms the results given hereinbefore in experiments on the mesenterial vein in rats.

The following Examples are intended to illustrate the invention:

EXAMPLE 1

Capsules as an Instant Formulation Containing Dipyridamole and Acetylsalicylic Acid Preparation:

a.) Dipyridamole granules 35 kg of dipyridamole, 30 kg of fumaric acid and 5 kg of polyvinylpyrrolidone are mixed for 15 minutes in a cube mixer. 0.4 kg of magnesium stearate is added and the mixture is stirred for a further 5 minutes.

The mixture is passed through a roller compactor, adjoining which is a dry granulating apparatus with screening mechanism. The fraction with a diameter of 0.4 to 1.0 mm is used.

b.) Acetylsalicylic acid coated tablets 35 kg of crystalline acetylsalicylic acid is mixed with 3.3 kg of flowable lactose, 12.5 kg of microcrystalline cellulose, 9 kg of dried corn starch and 0.5 kg of aluminium stearate in a cube mixer for 15 minutes and then compressed to form biconvex tablets weighing 90 mg with a diameter of 5.5 mm.

These cores are coated in several steps with a coating suspension consisting of 5.6 kg of sucrose, 0.5 kg of gum arabic and 3.8 kg of talc until the tablets weigh 110 mg. The coated tablets are thoroughly dried.

Filling

In a special capsule making machine the quantity of granules containing 175 mg of dipyridamole is packed into a hard gelatin capsule, size 1, and then the coated tablet containing 35 mg of acetylsalicylic acid is placed on top. The weight ratio of dipyridamole to acetylsalicylic acid is 5.

EXAMPLE 2

Capsules Containing Delayed-Release Dipyridamole Formulations Together With a Coated Tablet Containing Acetylsalicylic Acid a.) Dipyridamole pellets with delayed release of the active substance 300 kg of rounded tartaric acid starter pellets is sprayed, in a special pan, with a suspension consisting of isopropanol, dipyridamole and polyvinylpyrrolidone until the resulting pellets of active substance contain about 45% dipyridamole.

These pellets are sprayed with a lacquer consisting of methacrylic acid/methyl methacrylate copolymer (brand name Eudragit S) and hydroxypropylmethylcellulose phthalate (brand name HP 55) in a weight ratio of 85:15 to 50:50. The organic lacquer solutions also contain plasticiser and talc. Two pellet components are sprayed with 5 and 7% of coating and different ratios of the lacquer components within the limits specified. The two components are mixed together to give the following release in vitro:

Conditions: corresponding to US P XXI, basket method, 100 rpm.

1 hour in artificial gastric juice, 2 to 6 hours in artificial intestinal juice (phosphate buffer pH 5.5)

| Time | Percentage release of active substance per hour |
|---|---|
| 1st hour | approx. 30% |
| 2nd hour | approx. 25% |
| 3rd hour | approx. 18% |
| 4th hour | approx. 12% |
| after the 6th hour more than 90% of the dipyridamole has been released. | | b.) Coated tablets containing acetylsalicylic acid

As described in Example 1, acetylsalicylic acid cores weighing 100 mg are prepared by compressing the following mixture:

| | |
|---|---|
| Acetylsalicylic acid | 25.0% by weight |
| Lactose | 53.0% by weight |
| Microcrystalline cellulose | 11.0% by weight |
| Dried corn starch | 8.6% by weight |
| Silicon dioxide | 3.0% by weight |
| Aluminium stearate | 0.4% by weight |

These cores are coated, in the manner described, with the coating suspension specified until after thorough drying they weigh 120 mg.

c.) Filling:

in a special capsule making machine, the quantity of pellet corresponding to 200 mg of dipyridamole and a coated tablet containing 25 mg of acetylsalicylic acid are packed into a capsule, size 0.

The weight ratio of dipyridamole to acetylsalicylic acid is 8.

EXAMPLE 3

Capsules Containing a Delayed Release Dipyridamole Formulation Together With a Coated Tablet Containing Acetylsalicylic Acid a.) Dipyridamole pellets with delayed release of the active substance A powdered mixture containing dipyridamole and an organic solvent are metered into a double screw extruder in the correct ratio and mixed together. The moistened mass is extruded in the form of spaghetti which is rounded off in a container with a rapidly rotating base plate to produce highly compressed pellets. The pellets are then dried in a drying cupboard.

Composition of powder:

| | |
|---|---|
| Dipyridamole | 69.0% by weight |
| Ethyl cellulose | 5.5% by weight |
| Highly polymeric hydroxypropyl-methyl cellulose | 12.5% by weight |
| Polyethylene glycol 6000 | 1.0% by weight |
| Fumaric acid | 12.0% by weight | b.) Acetylsalicylic acid coated tablets

As described in Examples 1 and 2, a coated acetylsalicylic acid tablet weighing 75 mg and containing 5 mg of this substance is produced using the same excipients.

c.) Filling

In a special capsule making machine, a quantity of pellets containing 450 mg of dipyridamole and a coated tablet containing 5 mg of acetylsalicylic acid are packed into a capsule, size 00.

The weight ratio of dipyridamole to acetylsalicylic acid is 90.

EXAMPLE 4

Three-Layer Tablet

For a 3-layer tablet 3 granulates are produced:

a.) Dipyridamole granulate

A powdered mixture of 80% dipyridamole, 10% hydroxypropyl methylcellulose (highly polymeric) and 9% hydroxypropylcellulose (highly polymeric) is moistened with ethanol in a granulating apparatus and granulated through a screen with a mesh size of 1.5 mm. After drying and screening, 0.5% magnesium stearate is added (the percentages refer to % by weight).

b.) Separating granulate

A mixture of 50% lactose and 45% microcrystalline cellulose is moistened with 4.5% polyvinylpyrrolidone dissolved in water. The granulate, passed through a screen with a mesh size of 1 mm, is dried and mixed with 0.5% aluminium stearate (percentages given are % by weight).

c.) Acetylsalicylic acid granulate

80% flowable acetylsalicylic acid crystals are mixed with 15% of flowable lactose, 4.5% microcrystalline cellulose and 0.5% aluminium stearate (percentages refer to % by weight).

d.) Three-layer tablet

The granulates are fed into a special tablet press with 3 filling hoppers and 3 compressing stations in such a way that a tablet is formed containing 400 mg of dipyridamole and 80 mg of acetylsalicylic acid. The neutral layer between the two active substances weighs 50 mg. The oblong tablet (17×6.8 mm) is thoroughly dusted, dried and sealed in aluminium/aluminium blister packs.

The weight ratio of dipyridamole to acetylsalicylic acid is 5.

EXAMPLE 5

Capsules as an Instant Formulation Containing Dipyridamole and Acetylsalicylic Acid Preparation a.) Dipyridamole granulate A mixture of 30% dipyridamole, 63% fumaric acid and 6% polyvinylpyrrolidone is moistened with ethanol and passed through a screen with a mesh size of 1.5 mm. After drying, 1% magnesium stearate is added and the granulate is compressed in a roller compactor equipped with a dry granulating apparatus with screening mechanism. The fraction with a particle size of 0.4 to 1.25 mm is reused (percentages given are % by weight).

b.) Filling

In a special capsule making machine, the quantity of granulate corresponding to 100 mg of dipyridamole and a coated tablet containing 5 mg of acetylsalicylic acid according to Example 3 are packed into a capsule, size 0.

The release of active substance from the granules containing dipyridamole is independent of the pH:

| pH of artificial gastric or intestinal juice | invitro release of dipyridamole in minutes* | |
|---|---|---|
| | 50% | 90% |
| 1.2 | 3 | 11 |
| 4.0 | 4 | 13 |
| 6.0 | 4 | 15 |

*USP XXI paddle method 100 rpm

The weight ratio of dipyridamole to acetylsalicylic acid is 20.

EXAMPLE 6

Capsules as an Instant Formulation Containing Mopidamol and Acetylsalicylic Acid Preparation a.) Mopidamole granules 35 kg of mopidamol, 20 kg of fumaric acid and 5 kg of polyvinylpyrrolidone are mixed for 15 minutes in a cube mixer. 0.4 kg of magnesium stearate is added and the mixture is stirred for a further 5 minutes.

The mixture is passed through a roller compactor adjoining which is a dry granulating apparatus with screening mechanism. The fraction with a diameter of 0.4 to 1.0 mm is used.

b.) Acetylsalicylic acid coated tablets 35 kg of crystalline acetylsalicylic acid is mixed for 15 minutes with 3.3 kg of flowable lactose, 12.5 kg of microcrystalline cellulose, 9 kg or dried corn starch and 0.5 kg of aluminium stearate in a cube mixer for 15 minutes and then compressed to form biconvex tablets weighing 90 mg with a diameter of 5.5 mm.

These cores are coated in several steps with a coating suspension consisting of 5.6 kg of sucrose, 0.5 kg of gum arabic and 3.8 kg of talc until the tablets weigh 110 mg. The coated tablets are thoroughly dried.

c.) Filling

In a special capsule making machine the quantity of granulate corresponding to 210 mg of mopidamol is packed into a hard gelatin capsule, size 1, and then the coated tablet containing 35 mg of acetylsalicylic acid is placed on top. The weight ratio of mopidamol to acetylsalicylic acid is 6.

What is claimed is:

1. A pharmaceutical composition for oral administration comprising:
    a first component selected from the group consisting of dipyridamole, and the pharmaceutically acceptable salts thereof; and
    a second component selected from the group consisting of acetylsalicylic acid and the pharmaceutically acceptable salts thereof;
    said first and second components being present in a weight ratio in the range between 8:1 and 100:1;
    a pharmaceutically acceptable acid excipient formulated together with said first component in the form of granules provided with a coating made up of 50 to 100% of lacqueurs which are insoluble in acid but soluble in intestinal juices and 50 to 0% of lacqueurs which are insoluble in both gastric and intestinal juices, and said acid excipient being in a ratio of at least one equivalent of said acid excipient to 1 mol of said first component;
    said second component being present in the form of a tablet; and
    all components being contained together within a capsule.

2. A pharmaceutical composition for oral administration comprising:
    a first component selected from the group consisting of dipyridamole, and the pharmaceutically acceptable salts thereof; and
    a second component selected from the group consisting of acetylsalicylic acid and the pharmaceutically acceptable salts thereof;
    said first and second components being present in a weight ratio in the range between 8:1 and 100:1;
    a pharmaceutically acceptable acid excipient formulated together with said first component in the form of pellets provided with a coating made up of 50 to 100% of lacqueurs which are insoluble in acid but soluble in intestinal juices and 50 to 0% of lacqueurs which are insoluble in both gastric and intestinal juices, and said acid excipient being in a ratio of at least one equivalent of said acid excipient to 1 mol of said first component;
    said second component being present in the form of a tablet; and
    all components being contained together within a capsule.

3. The pharmaceutical composition of claim 1 wherein said acid excipient is selected from fumaric acid, tartaric acid, citric acid, succinic acid and malic acid.

4. The pharmaceutical composition of claim 2 wherein said acid excipient is selected from fumaric acid, tartaric acid, citric acid, succinic acid and malic acid.

5. The pharmaceutical composition of claim 1 wherein said acid excipient is selected from fumaric acid and tartaric acid.

6. The pharmaceutical composition of claim 2 wherein said acid excipient is selected from fumaric acid and tartaric acid.

7. The pharmaceutical composition of claim 1 wherein the lacqueurs which are insoluble in acid but soluble in intestinal juices are selected from the group consisting of methacrylic acid/methacrylic acid ester copolymers, hydroxypropylmethylcellulose phthalate, cellulose acetate phthalate, ethylcellulose phthalate, hydroxypropylmethylcellulose succinate, cellulose acetate succinate, hydroxypropylmethylcellulose hexahydrophthalate, cellulose acetate hexahydrophthalate, hydroxypropylmethylcellulose trimellitate and the mixtures thereof, and the lacqueurs which are insoluble in both intestinal and gastric juices are based on lacqueurs selected from the group consisting of acrylate, methacrylate and mixtures thereof with up to 14% by weight of ethylcellulose.

8. The pharmaceutical composition of claim 2 wherein the lacqueurs which are insoluble in acid but soluble in intestinal juices are selected from the group consisting of methacrylic acid/methacrylic acid ester copolymers, hydroxypropylmethylcellulose phthalate, cellulose acetate phthalate, ethylcellulose phthalate, hydroxypropylmethylcellulose succinate, cellulose acetate succinate, hydroxypropylmethylcellulose hexahydrophthalate, cellulose acetate hexahydrophthalate, hydroxypropylmethylcellulose trimellitate and the mixtures thereof, and the lacqueurs which are insoluble in both intestinal and gastric juices are based on lacqueurs selected from the group consisting of acrylate, methacrylate and mixtures thereof with up to 14% by weight of ethylcellulose.

9. The pharmaceutical composition of claim 1 wherein the coating of the granules is made up of methacrylic acid/methacrylic acid ester copolymer and hydroxypropylmethylcellulose phthalate in a weight ratio of 85:15 to 50:50, and the coating of the tablet comprises sucrose.

10. The pharmaceutical composition of claim 2 wherein the coating of the pellets is made up of methacrylic acid/methacrylic acid ester copolymer and hydroxypropylmethylcellulose phthalate in a weight ratio of 85:15 to 50:50, and the coating of the tablet comprises sucrose.

11. The pharmaceutical composition of claim 1 wherein said first component is present in an amount between 75 and 400 mg and said second component is present in an amount of 5 to 80 mg.

12. The pharmaceutical composition of claim 2 wherein said first component is present in an amount between 75 and 400 mg and said second component is present in an amount of 5 to 80 mg.

13. A pharmaceutical composition for oral administration comprising:
    (a) a first component selected from dipyridamole and the pharmaceutically acceptable salts thereof; and
    (b) a second component selected from acetylsalicylic acid and the pharmaceutically acceptable salts thereof; and,
    wherein the quantities of the first and second components are adjusted so that the weight ratio between them is between 8:1 and 100:1.

14. A pharmaceutical composition for oral administration comprising:
    (a) dipyridamole; and,
    (b) acetylsalicylic acid;
    wherein the quantities of dipyridamole and acetylsalicylic acid are adjusted so that the final dosage form comprises 200 mg of dipyridamole and 25 mg of acetylsalicylic acid, and so that the weight ratio between them is 8:1.

15. A pharmaceutical composition for oral administration comprising:
   a) dipyridamole pellets, each such pellet having a core consisting of a pharmaceutically acceptable acid excipient, a first coating surrounding the core comprising dipyridamole and polyvinylpyrrolidone, and a lacquer coating, on top of the first coating, comprising methacrylic acid/methylmethacrylate copolymer and hydoxypropylmethylcellulose phthalate;
   b) an acetylsalicylic acid tablet, comprising an acetylsalicylic acid core and a coating comprising sucrose; and,
   c) a capsule, for containing the dipyidamole pellets and the acetylsalicylic acid tablet;
the quantities of the various components being adjusted so that the final dosage form comprises about 25 mg of acetylsalicylic acid and about 200 mg of dipyridamole.

16. A method for inhibiting the formation of venous and arterial blood clots, which comprises administering to a patient requiring inhibition of venous or arterial clot formation, a first drug selected from the group consisting of dipyridamole and the pharmaceutically acceptable salts thereof; and a second drug selected from the group consisting of acetylsalicylic acid and the pharmaceutically acceptable salts thereof; with said first and second drugs being administered in a weight ratio in the range between 8:1 and 100:1.

17. A method for inhibiting the occurrence of temporary ischaemic episodes which consists of carrying out the method of claim 16.

18. A method for inhibiting the occurrence of strokes of the type caused by a blood clot which consists of carrying out the method of claim 16.

19. A method for inhibiting the occurrence of cardiac infarctions which consists of carrying out the method of claim 16.

20. The method of claim 16 wherein the patient suffers from arteriosclerosis.

\* \* \* \* \*

UNITED STATES PATENT AND TRADEMARK OFFICE
Certificate

Patent No. 6,015,577                                                                 Patented: January 18, 2000

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Wolfgang Eisert, Beberach, Germany; Peter Gruber, Biberach, Germany; and Hans Weisenberger, Biberach, Germany.

Signed and Sealed this Eighth Day of September 2009.

*MICHAEL P. WOODWARD*
*Supervisory Patent Examiner*
*Art Unit 1615*